United States Patent [19]

Goodman et al.

[11] Patent Number: 5,109,849
[45] Date of Patent: May 5, 1992

[54] PERINATAL PULSE OXIMETRY SENSOR

[75] Inventors: David E. Goodman, San Francisco; Jessica A. Warring, Millbrae; Paul D. Mannheimer, San Mateo, all of Calif.

[73] Assignee: Nellcor, Inc., Hayward, Calif.

[21] Appl. No.: 482,827

[22] Filed: Feb. 21, 1990

Related U.S. Application Data

[60] Division of Ser. No. 264,196, Oct. 28, 1988, Pat. No. 4,938,218, which is a continuation-in-part of Ser. No. 217,080, Jul. 7, 1988, abandoned, and a continuation-in-part of Ser. No. 206,918, Jun. 13, 1988, abandoned, said Ser. No. 217,080, is a continuation of Ser. No. 935,060, Nov. 21, 1986, abandoned, which is a continuation of Ser. No. 644,051, Aug. 24, 1984, abandoned, which is a continuation-in-part of Ser. No. 527,726, Aug. 30, 1983, abandoned, said Ser. No. 206,918, is a continuation of Ser. No. 105,509, Oct. 5, 1987, which is a continuation of Ser. No. 941,540, Dec. 11, 1986, abandoned, which is a continuation of Ser. No. 789,580, Oct. 21, 1985, abandoned, which is a division of Ser. No. 644,051.

[51] Int. Cl.⁵ .............................................. A61B 5/0444
[52] U.S. Cl. ..................................... 128/633; 128/670; 128/698; 128/700; 128/736
[58] Field of Search ................................. 128/633–635, 128/664–666, 643, 670, 698, 700, 736

[56] References Cited

U.S. PATENT DOCUMENTS

| | | |
|---|---|---|
| 3,167,658 | 1/1965 | Richter . |
| 3,599,629 | 8/1971 | Gordy . |
| 3,602,213 | 8/1971 | Howell et al. . |
| 3,647,299 | 3/1972 | Lavallee . |
| 3,659,586 | 5/1972 | Johns et al. . |
| 3,704,706 | 12/1972 | Herczfeld et al. . |
| 3,769,974 | 11/1973 | Smart et al. . |
| 3,841,314 | 10/1974 | Page . |
| 3,983,866 | 10/1976 | Ulrich et al. . |
| 4,013,067 | 3/1977 | Kresse et al. . |
| 4,041,932 | 8/1977 | Fostick . |
| 4,091,803 | 5/1978 | Pinder . |
| 4,197,853 | 4/1980 | Parker . |
| 4,244,375 | 1/1981 | Farrar et al. . |
| 4,281,659 | 8/1981 | Farrar et al. . |
| 4,324,256 | 4/1982 | Vesterager . |
| 4,350,165 | 9/1982 | Striese . |
| 4,370,984 | 2/1983 | Cartmell . |
| 4,396,017 | 8/1983 | Delpy et al. . |
| 4,537,197 | 8/1985 | Hulka . |

FOREIGN PATENT DOCUMENTS

| | | |
|---|---|---|
| 671279 | 10/1963 | Canada . |
| 0072185A2 | 8/1982 | European Pat. Off. . |
| 0094749A3 | 4/1983 | European Pat. Off. . |
| 0104619A2 | 9/1983 | European Pat. Off. . |
| 0135840 | 4/1985 | European Pat. Off. . |
| 0285307 | 10/1988 | European Pat. Off. . |
| 1909882 | 9/1970 | Fed. Rep. of Germany . |
| 2517129 | 6/1976 | Fed. Rep. of Germany . |
| 2830412 | 1/1980 | Fed. Rep. of Germany . |
| 9001293 | 2/1990 | World Int. Prop. O. . |

OTHER PUBLICATIONS

Article entitled "A New Fetal Scalp Electrode", Robert C. Goodlin and Stephen J. Fabricant, *Obstetrics and Gynecology*, vol. 35, No. 4, Apr. 1970.

Article entitled "Systolic Time Intervals in the Fetus and Neonate", Robert C. Goodlin, John Girard and

(List continued on next page.)

*Primary Examiner*—Ruth S. Smith
*Attorney, Agent, or Firm*—Townsend and Townsend

[57] ABSTRACT

An apparatus for use in measuring fetal blood flow characteristics. The apparatus includes a non-invasive pulse oximetry probe that is inserted into the uterus between the fetus and the uterine wall. The probe is deformable and is positively attached to the fetal tissue surface using a vacuum pump which causes the probe to deform from a pre-set curvature to the curvature of the fetal tissue surface and to form a gasket-type seal with the fetal tissue surface. The probe is manually inserted into the uterus using a curved insertion tool, and is shaped to fit through a slightly dilated cervix. In a preferred embodiment, the probe includes fetal and maternal ECG sensors and additional sensing devices, and is provided with apparatus for improving the efficiency of the pulse oximetry optics.

18 Claims, 9 Drawing Sheets

OTHER PUBLICATIONS

Arno Hollmen, *Obstetrics and Gynecology*, vol. 39, No. 2, Feb. 1972.

Article entitled "Intrapartum Fetal Heart Rate Responses and Plethysmographic Pulse", Robert C. Goodlin, *American Journal Obstetrics and Gynecology*, vol. 110, No. 2, May 15, 1971.

Article entitled "Care of the Fetus", Robert C. Goodlin, Masson Publishing, New York, 1979.

Article entitled "Near Infrared Spectrophotometry: A New Technique for Assessing Fetal Hypoxia", John W. Seeds et al., *Surgical Forum*, Gynecology and Obstetrics, 1982.

Article entitled "Noninvasive, Infrared Monitoring of Cerebral and Myocardial Oxygen Sufficiency and Circulatory Parameters", F. F. Jobsis, *Science*, 1977.

Article entitled "The Relationship of Intracranial Infrared Light Absorbance to Fetal Oxygenation", John W. Seeds et al., *American Journal of Obstetrics and Gynecology*, vol. 149, No. 6, Jul. 15, 1984.

Article entitled "The Fetal EEG (Detection of Oxygen Deprivation)", David A. Viniker, *British Journal of Hospital Medicine*, Nov. 1979.

Data Sheet, EG&G Electro-Optics, "Silicon Diffused Pin Photodiodes", SGD Series.

Data Sheet, United Detector Technology (UDT), "Planar Diffused Silicon Pin Photodiodes".

Data Sheet, Silicon Detector Corporation (SDC), "General Purpose Detectors".

Goodlin, R. C., Intrapartum Fetal Heart Rate Responses and Plethysomographic Pulse, *Amer. J. Obstet. Gynec.* 1971; 110:210.

Goodlin, R. C., Fabricant, S. J., A New Fetal Scalp Electrode, *Obstet. Gynecol.*, 1970; 35:646.

Goodlin, R. C., Girard J., Hollmen, A., Systolic Time Intervals in the Neonate, Obstet. Gynecol. 1972; 39:295.

Viniker, D. A., The Fetal EEG (Detection of Oxygen Deprivation), *British Journal of Hospital Medicine*, Nov. 1979; 504-510.

Weller, C. et al., Fetal Electroencephalography Using a New, Flexible Electrode, *British Journal of Obstetrics and Gynecology*, Oct. 1981; 88:983-986.

Silicon Detector Corporation ("SDC"), Data Sheet, General Purpose Detectors.

EG&G Electro Optics, Data Sheet, "Silicon Diffused Pin Photodiodes, SGD Series".

United Detector Technology ("UDT"), Data Sheet, Planar Diffused Silicon Pin Photodiodes.

Seeds, J. W., Celfalo, R. C., Near Infrared Spectrophotometry: A New Technique for Assessing Fetal Hypoxia, *Surg. Forum* 1982; 33:481.

Jobsis, F. F., Noninvasive, Infrared Monitoring of Cerebral and Myocardial Oxygen Sufficiency and Circulatory Parameters, *Science* 1977; 198:1264.

Goodlin, R. C., Fetal Heart Rate Monitoring, In: Goodlin, R. C., *Care of the Fetus*, New York:Masson Publishing, 1979:101-110.

Seeds, J. W., Cefalo, R. C. et al., The Relationship of Intracranial Light Absorbance to Fetal Oxygenation, *Am. J. Obstet. Gynec.* 1984; 149:679.

PERINATAL PULSE OXIMETRY SENSOR

REFERENCE TO PRIOR APPLICATIONS

This application is a divisional of commonly assigned U.S. Ser. No. 264,196, filed Oct. 28, 1988, now U.S. Pat. No. 4,938,218 issued Jul. 3, 1990, entitled IMPROVED PERINATAL PULSE OXIMETRY SENSOR. U.S. Ser. No. 264,196, now U.S. Pat. No. 4,938,218 is a continuation-in-part of application Ser. No. 217,080, filed Jul. 7, 1988 now abandoned, and application Ser. No. 206,918 filed Jun. 13, 1988 now abandoned. Application Ser. No. 217,080 is a continuation of application Ser. No. 935,060, filed Nov. 21, 1986 and now abandoned, which is a continuation of application Ser. No. 644,051, filed Aug. 24, 1984 and now abandoned, which is a continuation-in-part of application Ser. No. 527,726, filed Aug. 30, 1983 and now abandoned. Application Ser. No. 206,918 is a continuation of application Ser. No. 105,509, filed Oct. 5, 1987, which is a continuation of application Ser. No. 941,540, filed Dec. 11, 1986 and now abandoned, which is a continuation of application Ser. No. 789,580, filed Oct. 21, 1985 and now abandoned, which is a divisional of the above-referenced application Ser. No. 644,051.

BACKGROUND OF THE INVENTION

The present invention relates to a non-invasive pulse oximetry intrauterine sensor.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which passes light through a portion of the patient's tissue where blood perfuses the tissue, and photoelectrically senses the absorption of light in such tissue. The amount of light absorbed is then used to calculate the amount of blood constituent being measured.

The light passed through the tissue is selected to be of one or more wavelengths that are absorbed by the blood in an amount representative of the amount of the blood constituent present in the blood. The amount of transmitted light passed through the tissue will vary in accordance with the changing amount of blood constituent in the tissue and the related light absorption. For measuring blood oxygen level, such sensors have been provided with two sets of light sources and photodetectors that are adapted to operate at different wavelengths, in accordance with known techniques for measuring blood oxygen saturation.

Known non-invasive sensors include devices that are secured to a portion of the body, such as a finger, ear or the scalp. In animals and humans, the tissue of these body portions is perfused with blood and the tissue surface is readily accessible to the sensor.

It is desirable that photoelectric pulse oximetry also be useful for monitoring the blood flow characteristics and constituents of a fetus. For example, monitoring fetal oxygen levels provides an effective way to detect and provide indications for treating hypoxia in the fetus during labor. However, known sensors adapted for use on infants or adults are not suited for intrauterine placement.

The environment in which the non-invasive intrauterine sensor must operate is fluid-filled (e.g., by amniotic fluid) and is only accessible through the restricted opening of the cervix. Visual inspection of the fetus and the sensor is likewise restricted. Moreover, the operating environment presents certain variants that interfere with detection of the fetal blood flow characteristics using known pulse oximetry techniques. For example, the presence of the waxy vernix caseosa, hair, mucus, blood and dead tissue cells on top of the fetal tissue surface against which the sensor is to be positioned create a problem in establishing contact between the optical components of the sensor and the surface of blood-perfused tissue. Detection of fetal blood flow characteristics by pulse oximetry is particularly complicated by the relatively low perfusion and low oxygen saturation of blood in fetal tissue. These environmental factors prevent known sensors from providing reliable information needed to calculate fetal blood characteristics.

It is known that positive attachment of a sensor to the tissue improves the quality of the photoelectric signal provided by the sensor. Positive attachment to a human's tissue may be obtained by vacuum, adhesives, tapes or devices such as clothespin-type clips. However, fetal tissue is relatively moist and there is limited access to the tissue surface. Consequently, conventional adhesives or tapes or clips are not adapted for intrauterine use.

Known techniques involving invasive attachment to fetal tissue, such as by a screw attachment penetrating the tissue, creates a risk that the fetus will suffer an infection or disfigurement. Non-invasive attachment, such as by vacuum, may also result in disfigurement if the sensor includes sharp surfaces that press into the fetal tissue surface, or if the sensor is attached to the fetal tissue surface with excessive force (e.g., heavy vacuum suction).

Moreover, the intrauterine probe sensor must be safely and reliably deliverable to the point of contact with the fetus. It is desirable that intrauterine fetal monitoring be available early in labor, for example, to detect and treat hypoxia in the fetus during labor. Contact with the fetus can be made after natural rupture of the amniotic membrane by manually inserting a probe sensor into the uterus from the vagina, but access to the fetus through the vaginal canal is restricted by the cervix, which may be only slightly dilated to one or two centimeters when the membrane ruptures. Thus there is need for a fetal probe sensor that can be delivered to the fetus through a slightly dilated cervix, and a delivery system for doing so safely and reliably.

The present invention is directed to measurement of the fetal blood flow characteristics using a probe sensor adapted for intrauterine placement. The sensor can be adapted to operate in accordance with the photoelectric pulse oximetry measuring techniques described above as well as to accomplish other measurement techniques for monitoring the well-being of the fetus. For example, it is well known that electrical heart activity corresponding to the heartbeat can be monitored externally and characterized by the electrocardiogram ("ECG") waveform. The present invention contemplates that the ECG waveform of the fetus can be measured by providing the probe sensor with an ECG electrode which is in electrical contact with the fetus when the probe sensor is in place in the uterus. Further, the present invention contemplates that maternal blood flow characteristics and the maternal ECG waveform also can be measured by providing the probe sensor with one or more light sources, one or more photoelectric detectors and an ECG electrode directed toward the uterine wall.

The present invention also contemplates that the intrauterine probe sensor may include a thermistor to measure the temperature of the fetus, and a heat flux sensor to provide an indication of the adequacy of fetal tissue perfusion.

The present invention contemplates further that non-invasive positive attachment can be accomplished without disfigurement of the fetus by using a deformable probe sensor which is positively attached by creating a partial vacuum in a cavity formed in the probe to cause the probe to conform to the tissue surface of the fetus and to form a gasket-type seal with the fetal tissue surface.

SUMMARY OF THE INVENTION

The present invention provides an intrauterine probe sensor that can be inserted in the uterus shortly after rupture of the amniotic membrane and selectively positioned between a fetus and the uterine wall, the probe including connections for a vacuum source for creating a partial vacuum in the probe to positively attach the probe to the fetus, and electrical connections for connecting the probe sensor to equipment for powering the sensor and for evaluating the signal outputs of the sensor. In the preferred embodiment, the probe sensor is a pulse oximetry sensor and the cabling is electrical cabling for connecting the probe sensor to an external pulse oximeter.

The probe has a narrow, oblong body that permits the probe to be inserted through a slightly dilated cervix. The body of the probe includes one or more hollow cavities and is made of a flexible, inert biomaterial such as silicone rubber. The probe has a concave peripheral surface for attaching the probe to the fetus.

A gasket made of a material having greater compliancy than the fetal tissue surface is bonded to the concave peripheral surface of the probe. When the probe is positioned such that the gasket is adjacent the fetal tissue surface, a partial vacuum is created in one or more interior cavities of the probe, whereby the suction causes the probe body to deform and conform to the curvature of the fetal tissue surface. The gasket flattens outwardly to form a soft, substantially continuous area of contact with the fetus. A cream or gel sealant may be applied to the gasket to improve the seal between the gasket and the fetal tissue surface.

The partial vacuum is created in the interior cavity of the probe by connecting the probe cavity to a pump in a sump configuration. A vent tube connects the interior cavity of the probe to the open atmosphere, creating a constant flow of air through the probe to prevent clogging of the vacuum line and to control the vacuum pressure in the probe. Humid air or a saline solution also may be pumped through the probe to prevent the fetal tissue surface from becoming dry. A porous material such as open cell silicone foam is used in the interior cavity of the probe to prevent fetal tissue from being drawn into the vacuum port, and to diffuse the flow of air through the cavity.

The pump can be protected against contamination by a suction trap which contains filtering stages comprising hydrophobic filter elements to prevent passage to the pump of any fluid or airborne contaminants that have been evacuated from the probe, and which operates independently of the orientation of the suction trap. Alternatively, the suction trap may be replaced by filter elements in the vacuum line including an absorbent medium for absorbing fluid and a bacterial filter for removing contaminants from the air. In another alternative embodiment, the suction trap or serial in-line elements may be housed in a disposable cassette.

The probe includes a structure located in one or more interior cavities for supporting the sensor, preferably pulse oximetry optics. In a preferred embodiment, the optics, which include two or more light emitting diodes ("LEDs") for generating light at a plurality of selected wavelengths, and a photoelectric detector responsive to the wavelengths of light generated by the LEDs, are mounted on a flat substrate having electrical leads for connection to electrical cables extending outside of the uterus. The substrate can be lengthened, if desired, to permit the electrical leads to extend out of the uterus when the probe is in place, such that the connection between the leads and the electrical cable can be accomplished outside of the uterus.

The probe is configured to assure that an adequate amount of light passes from the light sources through the blood-perfused fetal tissue to the photodetector to provide a signal for measuring the fetal blood flow characteristics. An optical barrier is provided between the LEDs and the photoelectric detector to prevent light from passing from the LEDs directly to the photoelectric detector without traveling through the fetal tissue. In the preferred embodiment, a reflective material surrounding the LEDs and shaped for example as a cylindrical or parabolic reflector is provided to direct the light generated by the LEDs into the fetal tissue beneath the probe. A second reflector surrounding the photoelectric detector also is provided to direct light from the fetal tissue to the photoelectric detector and to prevent the detector from sensing shunted light. The optical barrier or either reflector may be formed of a conductive material and may operate as an ECG electrode. Alternately, a separate ECG electrode, which is spring-loaded to provide good electrical contact with the fetal tissue, may be provided.

The devices housed in the probe are mounted in a manner which protects the probe from the intrauterine environment, protects the fetal tissue surface from the probe, and imposes a contour on the fetal tissue surface in the vicinity of the optical devices to improve the consistency of measurement made by the sensor. For example, the probe can be provided with clear windows to cover and protect the optical devices. In a preferred embodiment, one or both of the windows have curved surface portions which, when brought into a contact with the fetal tissue surface, cause the tissue surface to dimple around the window. The dimpling effect thus created helps to prevent light from being shunted between the light source and photodetector devices and improves the coupling between the optical devices and blood-perfused fetal tissue. The perfusion of blood in the fetal tissue between the light source and the photodetector can be increased by creating a concave arc in the surface of the probe between the optical devices.

The probe may further be provided with optics and an ECG electrode for measuring maternal blood flow characteristics. The maternal ECG electrode may for example comprise a metallic button mounted on the surface of the probe body. In accordance with fetal ECG measurement techniques, the differential voltage between the fetal ECG electrode and the maternal ECG electrode can be used to determine the fetal ECG. In addition, other sensors such as a thermistor or a heat flux sensor or both may be provided, for example, to measure the temperature of the fetus and the perfusion of blood in the fetal tissue.

The probe body preferably also includes one or more receptacles for receiving an end portion of the insertion too. The insertion tool can be narrow, shaped member preferably comprising a flexible material formed into a single or double curve. The insertion tool preferably has a shaped end portion for insertion into one or more corresponding receptacles in the body of the probe to safely and reliably deliver the probe.

It is therefore an object of the present invention to provide an improved intrauterine probe sensor which can be positively attached to fetal tissue without risk of disfigurement of the fetus.

It is another object of the present invention to provide an improved fetal pulse oximetry sensor that efficiently couples light signals between the sensor and blood-perfused fetal tissue.

It is an additional object of the present invention to provide an improved fetal pulse oximetry sensor in which the sensor geometry imposes a contour on the fetal tissue surface in the vicinity of the optical devices of the sensor to improve the consistency of the oximetry measurements.

It is also an object of the present invention to provide an improved fetal oximetry sensor having a non-invasive fetal ECG electrode which also serves as an optical barrier and/or a reflector for improving the signal to noise radio of the light detected by the sensor.

It is yet a further object of the present invention to provide an improved intrauterine probe sensor having one or more spring-loaded ECG electrodes.

It is yet an even further object of the present invention to provide an intrauterine probe sensor that can be inserted in the uterus early in labor, and a delivery system for safely and reliably delivering the sensor to a desired location on the fetus.

BRIEF DESCRIPTION OF THE DRAWINGS

The above and other objects of and advantages of the present invention will be apparent upon consideration of the following detailed description, taken in conjunction with the accompanying drawings, in which like reference characters refer to like parts throughout, and in which.

DETAILED DESCRIPTION OF THE INVENTION

Figure 11A:
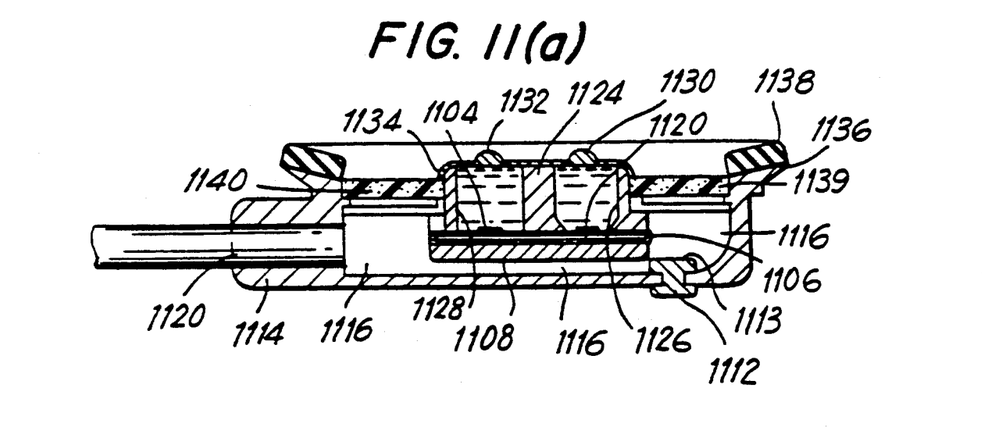
FIGS. 11(a)-(b) are top plan and cross-sectional side view of a preferred eighth embodiment of the probe of the present invention having protrusions over the light source and photodetector regions.
Figure 11B:
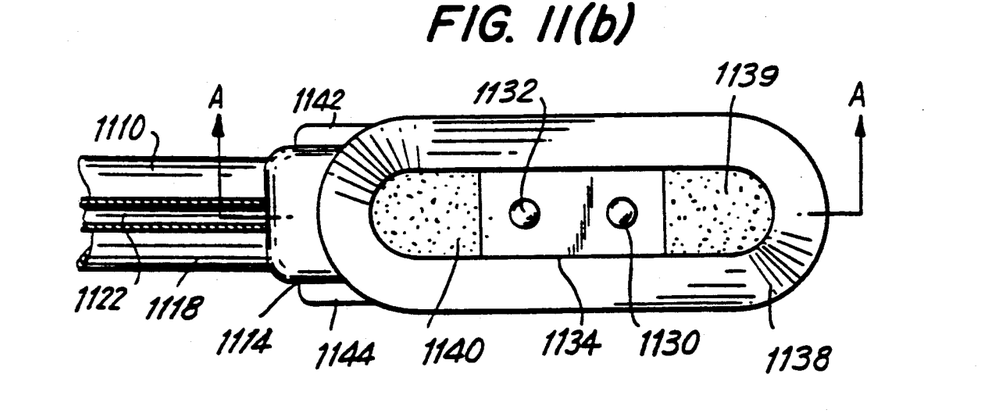

Various embodiments of the probe of the present invention are described herein and are shown in the figures. The preferred embodiment, which incorporates many features described in connection with other embodiments, is shown in FIGS. 11(a)-(b) and is described last.

Figure 1:
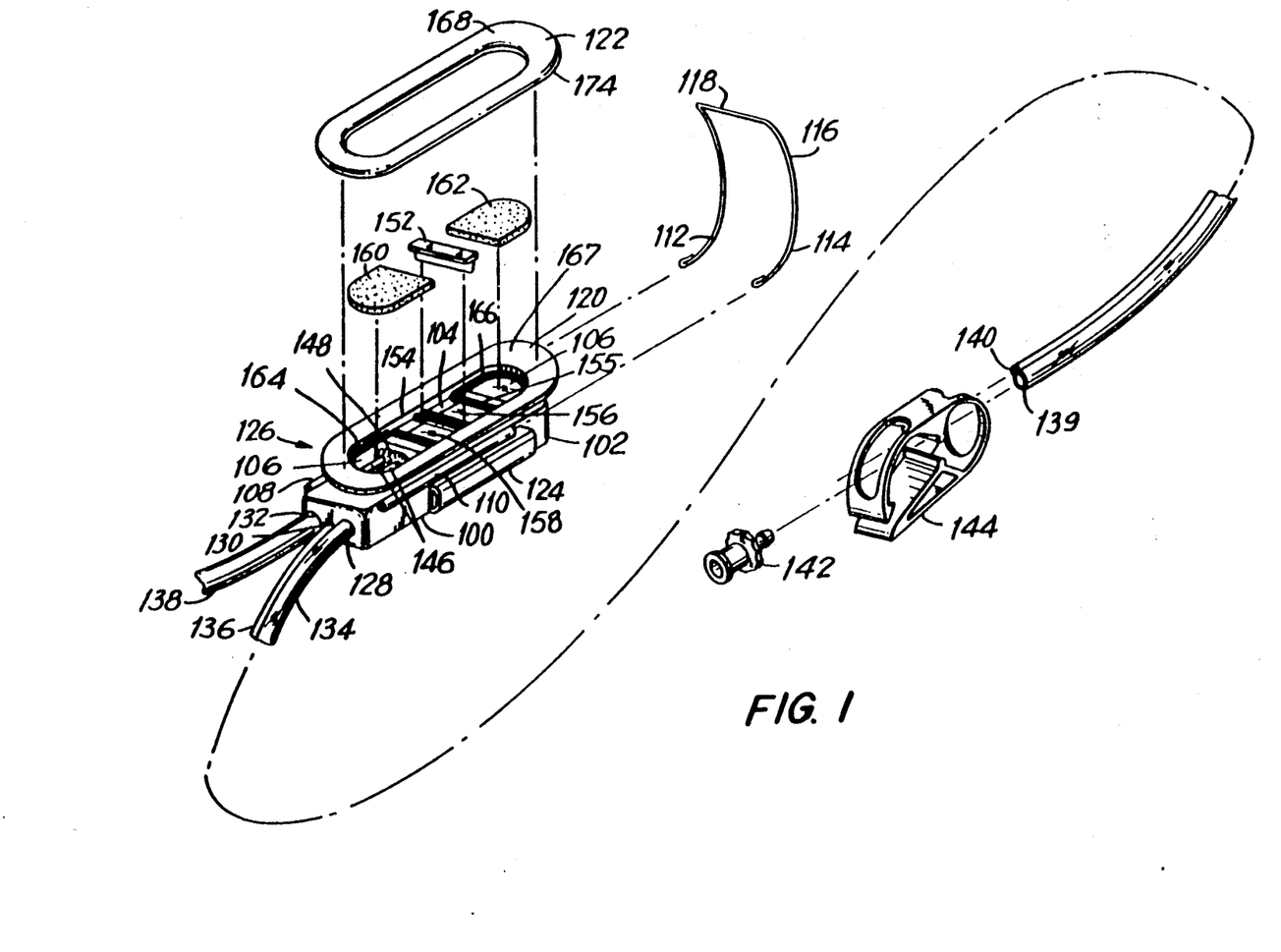
FIG. 1 is a partially-exploded elevated perspective view of a first embodiment of the probe sensor of the present invention.

Referring to FIG. 1, probe 100 comprises outer body 102 and inner boot 104 which house the photoelectric pulse oximetry measuring devices of the sensor. Inner boot 104 is shown apart from outer body 102 in FIG. 2(c). Outer body 102 is molded in a substantially rectangular, oblong shape, and has a hollow interior cavity 106 in which inner boot 104 is positioned.

Outer body 102 and inner boot 104 are molded or cast from a flexible, inert biocompatible material such as silicone rubber. The outer body is preferably made opaque, such as by addition of a coloring agent (e.g., white titanium dioxide). Inner boot 104, which encases the pulse oximetry optics, is preferably colored black to provide optical isolation between the probe's pulse oximetry light sources and photoelectric detector, which are described in greater detail below.

The height (or thickness) and width of outer body 102 are preferably sized to fit probe 100 through a cervix which is approximately 1-2 centimeters dilated, although a probe having a larger dimensions can of course be used after the cervix has become further dilated. Accordingly, the probe of the present invention has a slender appearance. A typical length of probe 100 is approximately 1.5 inches, although its length can be extended as necessary to encapsulate the electrical components of the probe (including electrical leads connected to those components) to isolate them from biological fluids. A typical height of probe 100 is 0.45 inches, and a typical width is 0.5 inches.

Outer body 102 has a pair of narrow channels 108 and 110 for receiving respectively legs 112 and 114 of U-shaped wire 116. Wire 116 forces outer body 102 to bend along its length in a concave curve defined by the strength of the wire, the curvature of legs 112 and 114 and the stiffness of probe 100. When legs 112 and 114 of wire 116 are inserted fully in channels 108 and 110, curved neck 118 of wire 116 abuts the underside of lip 120 of outer body 102, and is fixed in place by a flexible biocompatible adhesive. Wire 116 is formed from stainless steel, and is heat treated to harden the steel and to help maintain its form. With wire 116 in place, probe 100 has a concave curvature that preferably conforms approximately to the typical curvature of a fetal head. A typical value for the diameter of the fetal head is 4 inches.

The approximate conformance of the pre-set concave curvature of probe 100 to the fetal tissue surface allows a partial vacuum to be created in cavity 106 when gasket 122 of probe 100 is positioned against the fetal tissue surface and a negative pressure (vacuum) is applied to cavity 106. As described further below, the negative pressure causes gasket 122 bonded to lip 120 of outer body 102 to create a soft-contact seal with the fetal tissue surface. By providing the probe with a pre-set curvature that closely approximates the curvature of the fetal tissue surface, the amount of negative pressure required to deform probe 100 sufficiently to create the seal between gasket 122 and the fetal tissue surface is minimized. In this manner the contact between the probe and the fetal tissue surface is softened, and the risk of potential disfigurement caused by the positive attachment of the probe to the fetal tissue surface is minimized.

In an alternative embodiment of probe 100, outer body 102 may be molded with the desired concave curvature to eliminate the need for wire 116 and to increase the flexibility of outer body 102.

Outer body 102 further includes a pair of lengthwise receptacles 124 and 126 (not shown) for receiving the end portion of an insertion tool during insertion and placement of the probe in the uterus. Outer body also includes at one end conduits 128, 130 and 132 which receive respectively vacuum tube 134, vent tube 136 and electrical cable 138. Vacuum tube 134 and vent tube 136 are connected respectively via conduits 128 and 130 to cavity 106 to provide a partial vacuum in and a flow of air through cavity 106, and may comprise conventional double-lumen tubing. Hereafter, the partial vacuum created in the probe also is referred to simply as a "vacuum". The end 139 of vacuum pump (trap and pump not shown in FIG. 1). The end 140 of vent tube 136 is open to the atmosphere, such that when the pump is operated it draws air into vent tube 136 from the atmosphere and causes the air to pass through cavity 106 and into the suction trap via vacuum tube 134. A conventional quick-disconnect (or "Luer") connector 142 is provided for releasably connecting vacuum tube 134 to the suction trap, and a conventional clamp 144 is provided to clamp vacuum tube 134 when desired, such as during insertion, positioning and removal of probe 100.

Although vent tube 136 is not necessary to create a vacuum in cavity 106, it prevents vacuum tube 134 from becoming clogged by fluids and solid matter drawn into vacuum tube 134 from cavity 106.

The level of vacuum in cavity 106 is a function of the length and diameter of vacuum and vent tubes 134 and 136, and the flow rate of the vacuum pump. The vacuum in cavity 106 is maintained at a level which is sufficient to achieve positive attachment to the fetal surface. Because of the pre-set curvature and flexibility of outer body 102 and the compliancy of gasket 122 (discussed below), positive attachment can be achieved at a vacuum level which is not so high as to cause disfigurement of the fetal surface from the contact force of the probe. For example, positive attachment has been achieved using a diaphragm pump, set to a pressure within the range of 75-150 mmHg, with a 0.78 inch inner diameter vacuum tube 134 and a 0.020 inch inner diameter vent tube 136, both tubes being made of medical implant grade clear silicone and having equal length of approximately 3 feet.

In an alternative embodiment, humid air or a saline solution may be suctioned from a source connected to vent tube 136, through cavity 106 and into vacuum tube 134, to maintain a flow of liquid through cavity 106 for moistening the fetal tissue surface under probe 100.

Inner boot 104 supports a substrate 155 on which two light sources are mounted in light source region 156, and on which a photodetector is mounted in photodetector region 158. Regions 156 and 158 of the substrate are each coated by a thin layer of clear epoxy to protect the optical devices. Electrical connections to the light sources and photodetector from electrical cable 138 are provided by leads 146 which are electrically attached to the substrate. The exposed wire portions of leads 146 and the solder joints by which they are attached to the substrate are insulated by encapsulating the ends of inner boot 104 with silicone adhesive 148. Adhesive is also used to hold inner boot 104 in place in outer body 102.

The inner walls of outer body 102 that surround photodetector region 158 are coated with a layer of black silicone rubber to prevent shunting. Shunting occurs when light emitted by the light sources reaches the photodetector without first passing through fetal tissue. A flexible, black silicone rubber optical barrier 152 having a height when mounted approximately equal to the inner rim 154 of outer body 102 is provided between light source region 156 and photodetector region 158 to further optically isolate the photodetector from light generated by the light sources which does not pass through the fetal tissue. The optical barrier 152 preferably is formed from the same material as outer body 102 and inner boot 104, although other inert biomaterials may be used.

Light source region 156 and photodetector region 158 are each encapsulated by a clear layer (not shown) of epoxy or silicone rubber which has a height approximately equal to the inner rim 154 of outer body 102. These layers fill cavity 106 of outer body 102 above light source and photodetector regions 156 and 158 to provide light-transmissive surfaces for making contact with the fetal tissue surface.

Open cell silicone foam pads 160 and 162 are positioned over the exposed portions of cavity 106 and are bonded with adhesive, respectively, to U-shaped shelves 164 and 166 of outer body 102. The open-cell silicone foam diffuses the air drawn into cavity 106 from the vicinity of the fetal surface under probe 100 through numerous small vacuum ports formed by the open cell structure of the silicone foam. In this manner a vacuum is created over a large area without risk that a large piece of solid matter may be drawn into the vacuum line. The pads also prevent fetal tissue from being drawn into cavity 106 and damaged. Although open cell silicone foam pads are preferably because of their flexibility, more rigid materials such as porous plastic may also be used for filter pads 160 and 162.

Gasket 122 is bonded to the upper surface 167 of lip 120. Lip 120 thins as it extends outwardly and upwardly from the upper portion of outer body 102. Gasket 122 is shaped as a ring having a substantially flat top surface 168, which is elevated at outer edge 174 by lip 120. When probe 100 is in place and a vacuum is created in cavity 106, lip 120 and gasket 122 operate as a cantilever, bending outwardly and flattening to absorb the contact forces between probe 100 and the fetal tissue surface by distributing the forces in directions perpendicular to the fetal tissue surface.

The vacuum causes a seal to form between the fetal tissue surface and outer edge 174 of gasket 122. The vacuum created in cavity 106 is thus distributed over a large surface area to provide a substantially even attractive force over that area. As a result, a good seal can be obtained even where the fetal surface is covered by hair. As described in greater detail below, a sealant cream or gel may also be used if desired between gasket 122 and the fetal tissue surface to facilitate the formation of a seal which minimizes the likelihood of a continuous flow of biological fluid into cavity 106.

Gasket 122 is made from a soft material such as silicone rubber of silicone gel having a compliancy that is greater than that of the fetal tissue, so that when a vacuum is created in cavity 106, gasket 122 deforms before the fetal tissue to create a gasket-type seal. The deformation of gasket 122 allows the formation of a seal over fetal hair, and minimizes the risk that the fetal tissue will be marked or disfigured by probe 100.

Figure 2A:
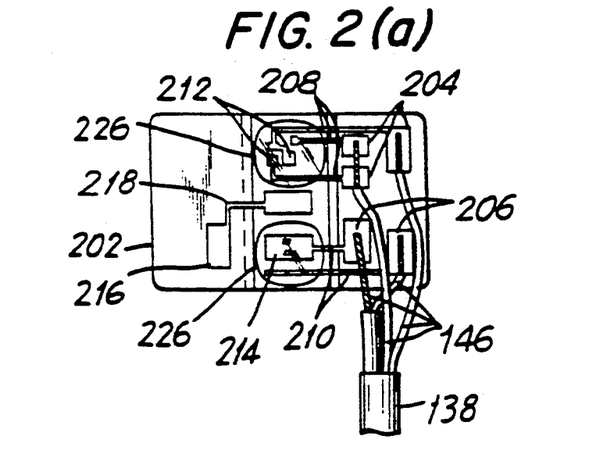
FIGS. 2(a)-2(c) are perspective views of the optics, electrical cable, substrate and inner boot of the probe or FIG. 1.
Figure 2B:
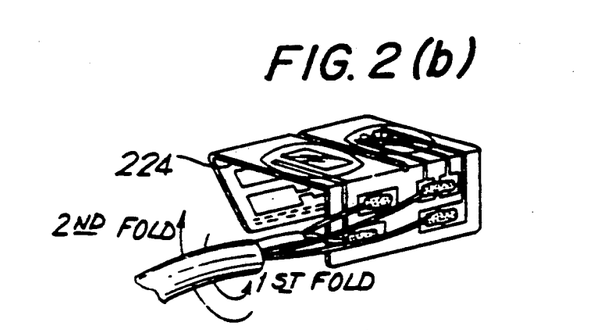
Figure 2C:
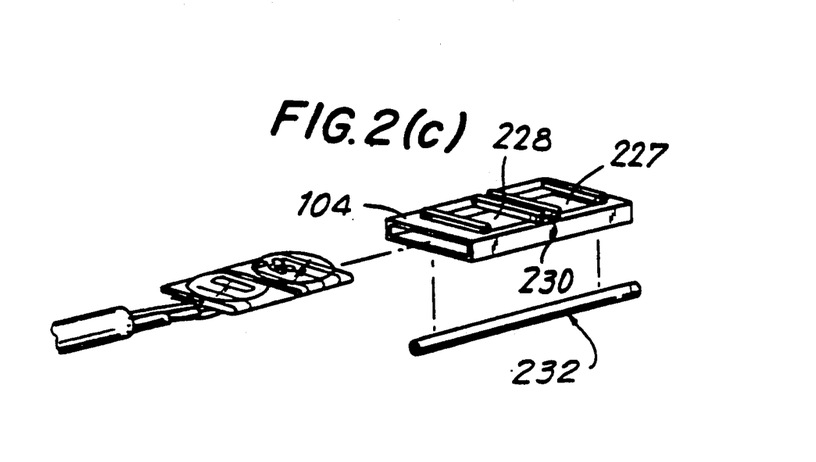

FIGS. 2(a)-2(c) show a typical assembly for mounting the pulse oximetry optics in probe 100. Substrate 202 comprises a thin layer of flexible insulating material such as polyamide film, one side of which is placed with solder pads 204 and 206 and conducting paths 208 and 210, preferably comprising layered metals such as copper, nickel and gold, for connecting wires 146 of electrical cable 138, respectively, to light sources 212 and photoelectric detector 214. The back of substrate 202 is copper-coated to prevent light from traveling through the substrate to the photodetector and a stiffener 224 is attached to the back of substrate 202 to provide support when electrical connections are made between the substrate and light sources 212 and photodetector 214. Solder pad 216 and conducting path 218 may be provided also for making electrical connections to a fetal ECG electrode (not shown in FIGS. 2(a)-2(c)).

Light sources 212 preferably comprise two or more LEDs, at least one of which has a nominal discrete frequency in the red light range, for example 660 nanometers (nm), and another having a nominal discrete frequency in the infrared range, for example 960 nm, in accordance with pulse oximetry techniques for measurement of oxygen saturation. Additional LEDs of different wavelengths may also be provided if desired to obtain information relating to factors such as tissue density or the average amount of blood in the tissue. To compensate for the relatively low level of oxygen saturation in the fetal blood, which creates a low signal to noise ratio in the red LED signal, it is preferred that a bright (e.g., 1.0 mW) red LED having zero secondary emission be used.

Photodetector 214 preferably comprises a photoelectric detector having discrete frequency responsivities at the different peak frequencies of the LEDs. The LEDs and the photodetector are mounted to substrate 202 using electrically conductive epoxy with additional electrical connections provided by wire bonding.

As described earlier, the light sources and photodetector are encapsulated with clear epoxy 226. The flexible substrate 202 is folded as shown in FIG. 2(b) to reduce its dimensions, and is inserted in inner boot 104. Inner boot 104 has two openings 227 and 228 which correspond respectively to light source region 156 and photodetector region 158. Slot 230 is formed in inner boot 104 between openings 226 and 228 to support optical barrier 152 (shown in FIG. 1). A silicone tube 232 is attached underneath inner boot 104 as a spacer to maintain an air flow channel between inner boot 104 and the rear inner surface of outer body 102 when a vacuum is created in cavity 106.

The mounting of the LEDs and the photodetector onto substrate 202 herein disclosed can be accomplished through other configurations. For example, a single layer substrate may be provided to reduce the height of the probe. To maintain a suitable surface area for mounting and making electrical connections to the LEDs and the photodetector without increasing the width of the probe 100, the length of the substrate can be extended in the direction of the longer dimension of the probe 100, with the solder pads being removed away from the LEDs and the photodetector, such that electrical connections to the substrate are made outside of outer body 102. This reduces the required height of outer body 102. The extended substrate and the electrical connections thereto can be electrically isolated from the biological fluids by encapsulation with silicone rubber. If desired, the encapsulated substrate can be extended to permit the electrical connections to be made outside the uterus when the probe is in position. Further, an integrated chip or a thin film constructions may be used if desired for mass production of either light sources 212 or photodetector 214. Alternatively, fiber optic connections between substrate 202 and the external pulse oximeter are also suitable.

The structure and arrangement of probe 100 is such that when the light sources are operating, the entire probe functions to assure that an adequate level of light is transmitted to a blood-perfused portion of the fetal skin despite the presence of hair, blood, mucus or other substances which tend to decrease the light level. As discussed below in connection with alternative probe embodiments, the transmission efficiency of the probe may be increased by supplementing one or both of the light sources and photodetector with means for focusing the transmitted light, and for imposing a contour on the fetal tissue surface to minimize shunting, maximize coupling through interfering substances and improve blood perfusion of the fetal tissue between the optical devices.

Figure 3:
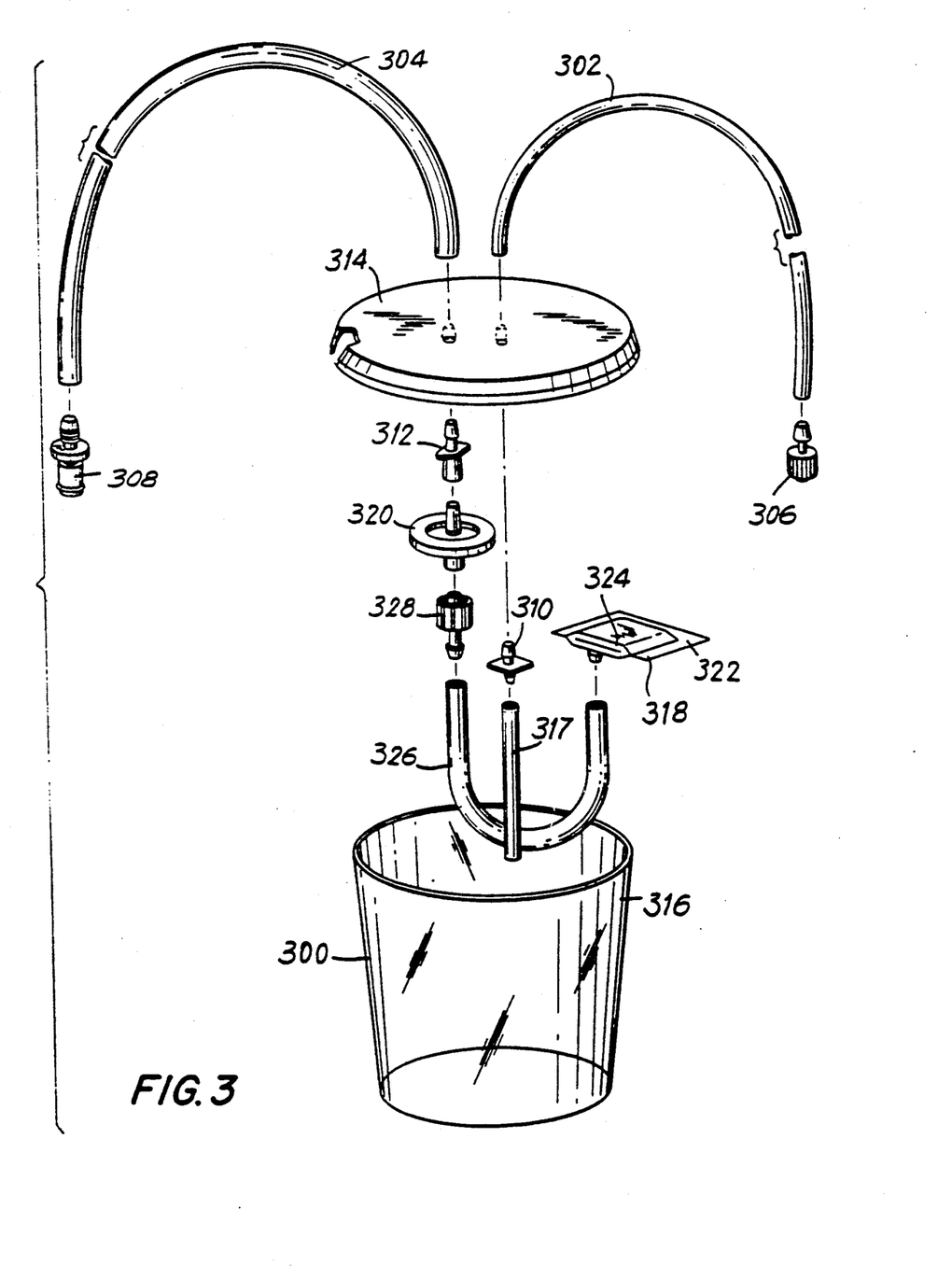
FIG. 3 is an exploded perspective view of an embodiment of a suction trap for use with the probe sensor of FIG. 1.

FIG. 3 is an exploded view of an embodiment of a suction trap 300 for handling fluids and solid matter drawn into vacuum tube 134 (shown in FIG. 1) and for removing contaminants from the air in vacuum tube 134 to prevent contamination of the vacuum pump. Intake tube 302 and outflow tube 304 comprise conventional silicone rubber tubing. Intake tube 302 and outflow tube 304 are connected respectively to connector 142 of vacuum tube 134 via conventional quick-disconnect connector 306 and to the air intake of the vacuum pump via pneumatic connector 308. Connectors 306 and 308 facilitate simple connection of suction trap 300, which also can be quickly disconnected for easy disposal. Intake tube 302 and outflow tube 304 are connected respectively via connectors 301 and 312 to plastic lid 314 of suction trap 300, which forms an air-tight seal with and is securely attached to plastic jar 316. A length of silicone tubing 317 is attached to connector 310 for passing air and fluids into jar 316 from intake tube 302.

Filters 318 and 320 respectively prevent fluid and solid matter from being drawn into outflow tube 304, and remove contaminants from the air that is drawn into outflow tube 304. Filter 318 comprises a hydrophobic filter surface, which is formed into a sealed pouch 322 and which encases a sponge 324. Sponge 324 causes filter 318 to float on any fluid collected in jar 316, and thereby prevents the hydrophobic filter surface from being entirely submerged in fluid, which would block the flow of air into outflow tube 304. Filter 318 is connected to a length of flexible silicone rubber tubing 326 which permits filter 318 to move freely about jar 316.

Filter 320, which is connected to tubing 326 by connector 328, and to outflow tube 304 by connector 312, comprises a hydrophobic bacterial filter having a pore size of approximately 0.2 microns.

Suction trap 300 is capable of removing fluids and air-borne contaminants from the air drawn into jar 316 independent of the orientation of jar 316. This permits suction trap 300 to be moved with the patient (the mother), and to be attached, for example, to the leg of the patient. The suction trap is disposable, and can be made opaque if desired for aesthetic purposes. The suction trap typically will be required to handle approximately 5-10 cc of fluid, and therefore can be made sufficiently small to be comfortably carried by the patient.

Alternatively, suction trap 300 can be replaced by one or more disposable in-line filters, including an absorbent medium for absorbing fluids in vacuum tube 134 and a bacterial filter for removing air-borne contaminants. Suction trap 300 or the in-line filters may be housed in a disposable cassette for mounting in a module connected to the vacuum pump and the intrauterine probe. The cassette may further include a rubber diaphragm which is punctured by a needle in the module to make a vacuum connection to the filters housed in the cassette.

Figure 4A:
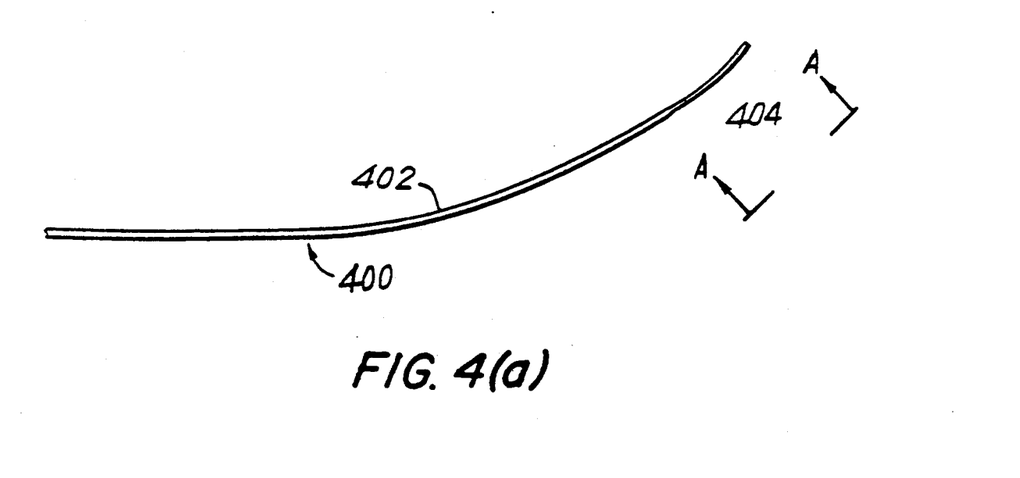
FIGS. 4(a)-(b) are perspective views of an embodiment of an insertion tool of the present invention.
Figure 4B:
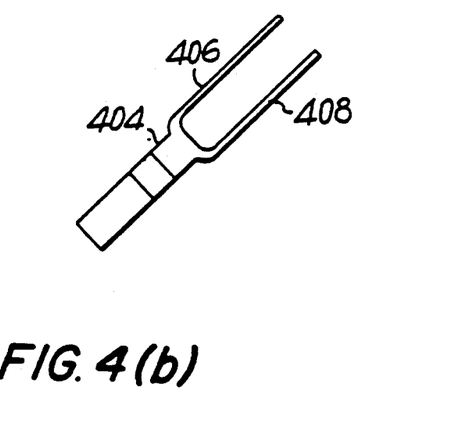

FIGS. 4(a)-(b) show an embodiment of an insertion tool 400 that can be used to safely and reliably position probe 100. Insertion tool 400 comprises a shaped plastic member having a curved body portion 402 and a forked end portion 404. Body portion 402 may be shaped in a single curve (as shown) or double curve as desired to facilitate insertion of the probe into the uterus. The forks 406 and 408 of end portion 404 are relatively flexible from side to side, and are relatively inflexible in directions perpendicular to the plane of insertion tool 400. Forks 406 and 408 are inserted into receptables 124 and 126 of probe 100 (shown in FIG. 1) to deliver the probe to the desired attachment site on the fetus. Insertion tool 400 permits probe 100 to be placed between the fetus and the uterine wall at a distance from the vaginal canal, thereby allowing the probe to be attached to a particular portion of the fetus such as the head, which may be turned away from the vaginal canal. In an alternative embodiment, the insertion tool may have a spatula-shaped end portion for insertion into a corresponding sleeve in the probe. The spatula end portion is useful if less flexibility from side to side than that possessed by the forked end portion is desired.

Figure 5:
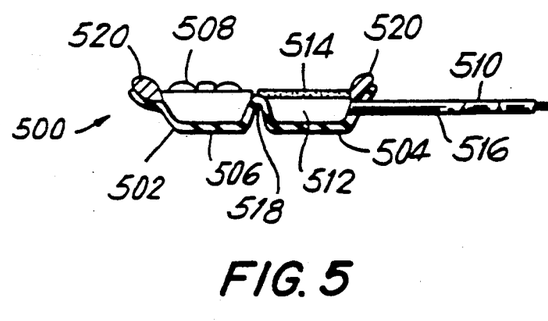
FIG. 5 is a cross-sectional side view of a second embodiment of the probe sensor of the present invention having a segmented outer body.
Figure 6:
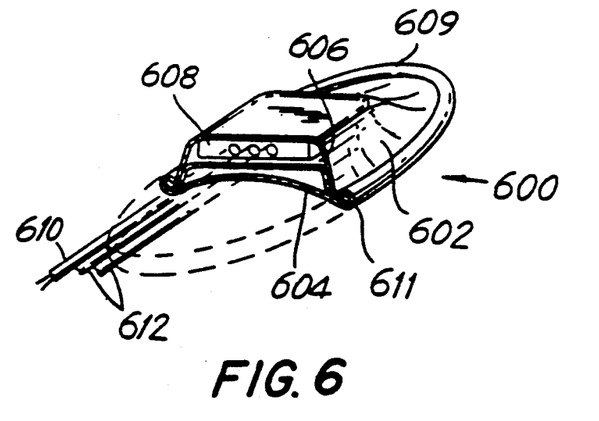
FIG. 6 is an elevated perspective view of a third embodiment of the probe sensor of the present invention having an outer body shaped as a thin diaphragm.

FIGS. 5-6 illustrate respectively second and third embodiments of the intrauterine probe of the present invention having different outer body structures for achieving flexibility. FIG. 5 shows an intrauterine probe 500 having first and second segmented sections 502 and 504 defined by silicone rubber outer body 506. First segmented section 502 houses fetal pulse oximetry optics 508, to which electrical connections are made by electrical cable 510. Second segmented section 504 forms a cavity 512 covered by open cell silicone foam filter pad 514. Cavity 512 is connected to double-lumen vacuum and vent tubes 516. When probe 500 is in place and air is suctioned from cavity 512, a vacuum is created between the fetal tissue surface and first and second segmented sections 502 and 504 which causes the outer body 506 to bend at juncture 518 of first and second segmented sections 502 and 504 as necessary to conform the curvature of gasket 520 to that of the fetal tissue surface and to form a seal with the fetal tissue surface. Although only two segmented sections are illustrated, outer body 506 may be divided into additional segmented sections to provide greater flexibility.

FIG. 6 shows an intrauterine probe 600 in which outer body 602 comprises a thin, flexible curved diaphragm 604 having a pocket 606 for supporting pulse oximetry and ECG sensor module 608. Outer edge 609 of diaphragm 604 is bonded to a gasket 611 for forming a seal with the fetal tissue surface like the gasket or probe 100 described above. Electrical cable 610 and double-lumen vacuum and vent tubes 612 connect to pocket 606 to establish electrical and pneumatic conduits to probe 600.

Referring now to FIGS. 7-11, fourth, fifth, sixth, seventh, and eighth embodiments of an intrauterine probe having different arrangements of sensing devices are illustrated.

Figure 7A:
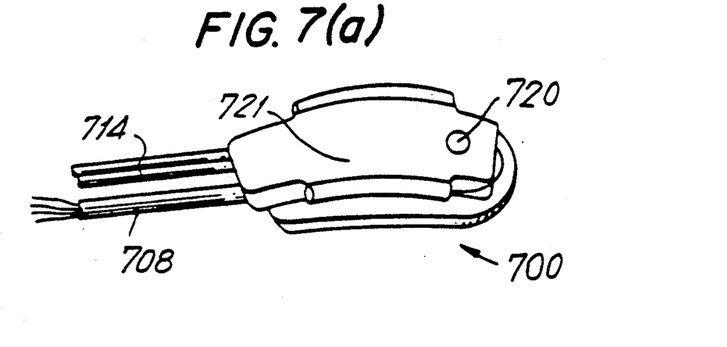
FIGS. 7(a)-(b) are top plan and bottom perspective views of a fourth embodiment of the probe sensor of the present invention including a fetal ECG electrode which also serves as an optical barrier.
Figure 7B:
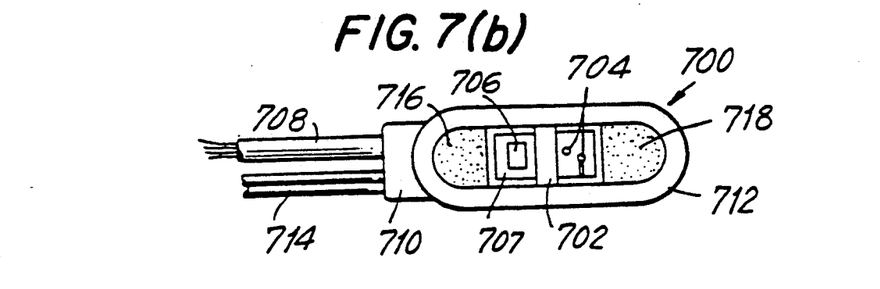

FIGS. 7(a)-(b) shows top and bottom views of an intrauterine probe 100 in which optical barrier 702 also serves as a fetal ECG electrode. The electrode is made from an electrically conductive material such as silver, stainless steel or conductive silicone which, with the probe in place, contacts the fetal tissue. The electrode is mounted between light sources 704 and photodetector 706 to serve the dual purpose of preventing light from shunting between the light sources and the photodetector, and of providing a conductive surface useful as an ECG sensor. The electrode is mounted on and electrically connected to substrate 707, on which the light sources and photodetector are mounted, using conductive adhesive or soldering. An electrical signal from the ECG electrode is provided to ECG monitoring equipment by electrical cable 708, which includes a wire electrically connected to the ECG electrode via the substrate and also provides electrical connections for light sources 704 and photodetector 706.

Probe 700 also includes a silicone rubber outer body 710 having a gasket 712 for creating a seal with the fetal tissue surface when a vacuum is created in outer body 710. Double-lumen vacuum and vent tube 714 provide pneumatic connections between the probe and a vacuum source (not shown). Open cell silicone foam filter pads 716 and 718 are provided to diffuse the flow of air and fluid in the probe, and to prevent fetal tissue from being drawn into and damaged by the vacuum cavity of the probe.

Probe 700 further includes a maternal ECG button 720 mounted flush with rear surface 721 of probe 700. Button 720 comprises an electrically conductive material such as silver or stainless steel, and is connected to a wire in electrical cable 708 for providing an ECG signal to ECG monitoring equipment. When probe 700 is in place, button 720 is in direct electrical contact with the uterine wall or with biological fluids in the uterus which convey to button 720 an electrical signal representative, at least in part, of maternal and fetal electrical heart activity. Button 720 may have any desired shape and be placed in any location on rear surface 721 useful for establishing electrical contact with the uterine wall or the biological fluid in the uterus. The signal detected by button 720 can be used, in conjunction with the signal detected by ECG sensor 702 in contact with the fetal tissue surface, to determine fetal electrical heart activity.

Applicants have discovered that the seal provided by gasket 712 serves the dual purposes of positively attaching the probe to the fetal tissue surface (without disfigurement and despite the presence of hair on the fetus, as discussed above in connection with probe 100), and of electrically insulating fetal ECG electrode 702 from maternal ECG electrode 720 to attenuate any undesirable interference or cross-talk between the two ECG electrodes caused by conductive biological fluids in the uterus. Gasket 712 preferably provides a seal that prevents biological fluids from forming a continuous electrical conduction path between the fetal and maternal ECG electrodes after the probe is in place. A gel-like or cream-like sealant may be used on the surface of gasket 712 to improve the seal formed by gasket 712 with the fetal tissue surface, or gasket 712 may be provided with an open channel in the surface thereof in which sealant can be disposed and applied to the fetal tissue surface to achieve the same effect.

Figure 8A:
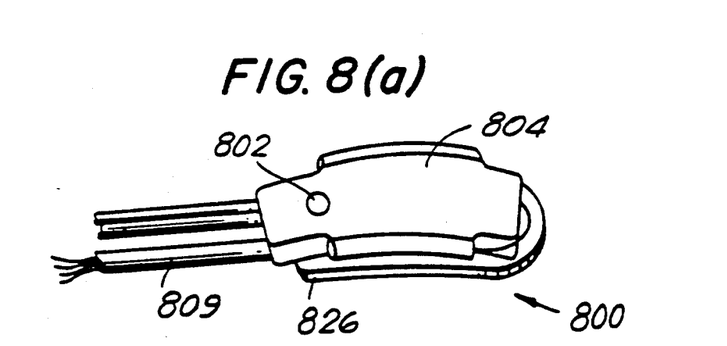
FIGS. 8(a)-(b) are top plan and bottom perspective view of a fifth embodiment of the probe sensor of the present invention including a fetal ECG electrode which also serves as an optical barrier and a reflector.
Figure 8B:
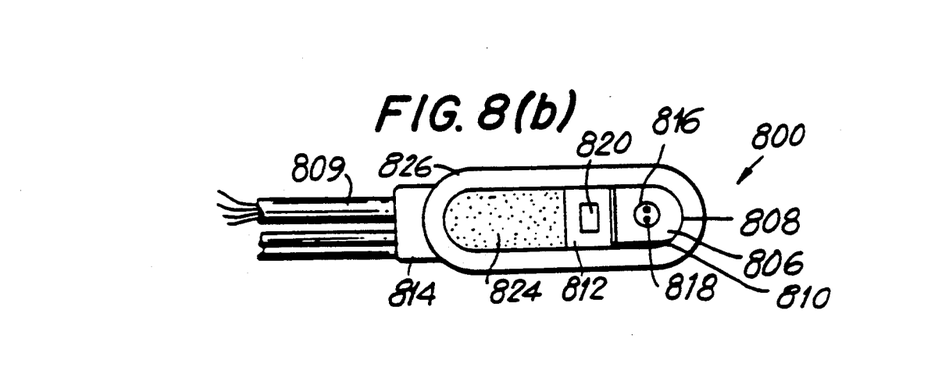

FIGS. 8(a)-(b) show top and bottom views of an intrauterine probe 800 having a maternal ECG electrode button 802 mounted flush with rear surface 804 of probe 800, and a fetal ECG electrode 806. Fetal ECG electrode 806 comprises a substantially rectangular block of electrically conductive material such as silver, stainless steel or conductive silicone. Electrode 806 has a curved end portion 808 which fits into the side of curved end portion 810 of outer body 814 of probe 800. Electrode 806 has a circular opening 816 which has optically reflective walls, and which is aligned directly above light sources 818. Circular opening 816 is filled with a clear encapsulant such as clear silicone rubber to reduce the possibility that the fetal tissue surface may be damaged by the hard edges of the circular opening, and the keep the circular opening free of material that might reduce the intensity of the light reaching the fetal tissue surface. The outer edges of electrode 806, as well as those of other metallic components of the intrauterine probes described in connection with alternative embodiments of the present invention, may be rounded to reduce the possibility of tissue damage. Electrode 806 is mounted on substrate 812 on which light sources 818 and photodetector 820 are mounted, and is electrically connected to the substrate by conductive epoxy. The electrode is connected via the substrate to a wire of electrical cable 808, which provides an electrical signal from the electrode to ECG monitoring equipment.

When probe 800 is in place, electrode 806 contacts the fetal tissue surface and serves the multiple purposes of preventing light from shunting between light sources 818 and photodetector 820, of focusing and directing light from light sources 818 toward the fetal tissue surface to increase the intensity of light passing through the fetal tissue, and of providing an electrically conductive surface suitable for detecting a fetal ECG signal.

Probe 800 is asymmetric in that ECG electrode 806, light source 818 and photodetector 820 are located at one end of the probe, and a porous filter pad 824 is located at the other end of the probe. In this manner, the relatively stiff components of probe 800, including the ECG electrode, light sources, photodetector and substrate, are located at one end of the probe, and do not straddle the midsection of the probe, thereby increasing the flexibility of the probe at its midsection to provide a good seal between gasket 826 and the fetal tissue surface.

Figure 9A:
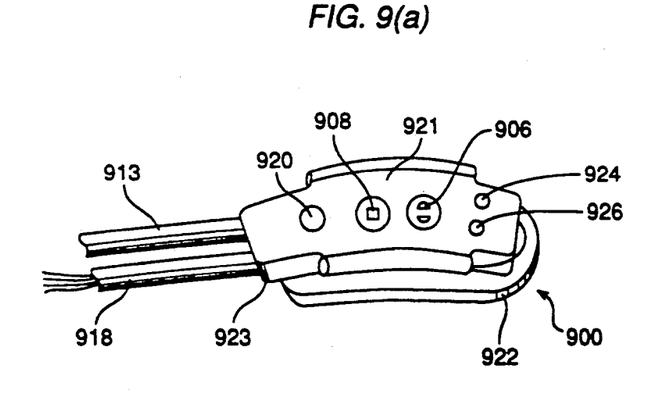
FIGS. 9(a)-(b) are top plan and bottom perspective views of a sixth embodiment of the probe of the present invention including two reflectors for increasing the efficiency of light transmission, and a spring-loaded fetal ECG electrode.
Figure 9B:
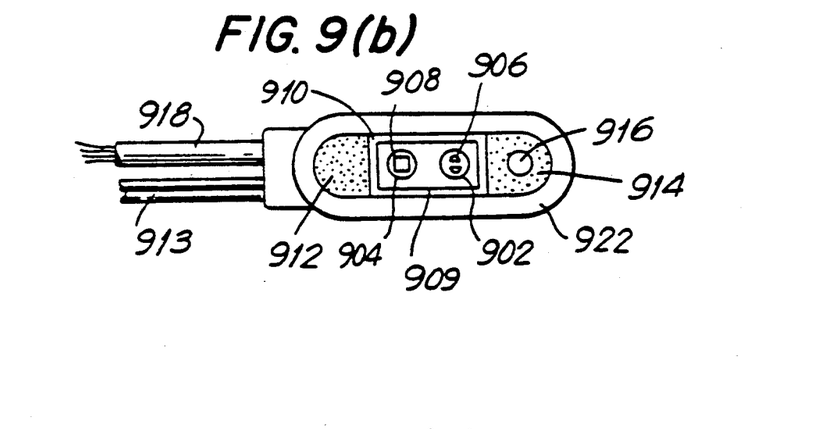

FIGS. 9(a)-(b) show top and bottom views of an intrauterine probe 900 in which individual reflectors 902 and 904 are mounted over light sources 906 and photodetector 908, respectively, to serve the multiple purposes of focusing the directing light from light sources 906 toward the fetal tissue surface, of minimizing the amount of shunted light detected by photodetector 908, and of focusing and directly light from the fetal tissue surface toward photodetector 908.

Reflectors 902 and 904 comprise metal parts having thin, circular walls with reflective inner surfaces, preferably shaped in the form of a cylinder or a paraboloid centered respectively on light sources 906 and a photodetector 908. Reflectors 902 and 904 are mounted on substrate 909 on which light sources 906 and photodetector 908 are mounted, and are filled with an encased in clear, soft silicone rubber 910 which minimizes the possibility of damage to the fetal tissue surface caused by the hard edges of the reflectors.

Open cell silicone foam filter pads 912 and 914 are attached to the probe to cover the remaining exposed portions of the cavity (now shown) of the probe. Double-lumen vacuum and vent tubes 913 provide pneumatic connections between the probe and a vacuum source (not shown). A fetal ECG electrode 916 comprising an electrically conductive material such as silver or stainless steel is attached to the surface of filter pad 914, such as by forcing the electrode through a hole in the filter pad, to provide a spring-loaded electrically-conductive surface for contacting the fetal tissue surface. A wire is connected to the back surface of electrode 916 and passed through filter pad 914 to electrical cable 918 for making electrical connection to electrode 916. When probe 900 is in place, electrode 916 is urged against the fetal tissue surface by the spring action of filter pad 914 to form a firm electrical contact useful for sensing the fetal ECG signal. This spring action also can be achieved if desired by using other types of conventional springs such as a coil spring or a cantilever spring.

In probe 900, the fetal ECG electrode 916 is electrically decoupled from the reflectors. Since the reflectors are not performing the function of an electrical contact, they can be formed from non-conductive materials softer than metal. For example, a block of flexible silicone rubber can be used to form the reflectors. The body of the block is made of black-colored silicone rubber to act as a light barrier between the light sources and photodetector, and includes two circular openings corresponding, respectively, to the light sources and the photodetector. The openings have a coating of reflective white-colored silicone rubber on their walls and are positioned to form cylindrical or parabolic reflectors over the light sources and photodetector. The openings can be filled with a clear encapsulant to reduce the possibility of interference caused by fluid or tissue that may reduce the intensity of light transmitted from the light sources through the fetal tissue surface to the photodetector. Alternately, separate flexible reflectors comprising layers of white and black-colored silicone rubber, or silicone rubber coated with a layer of reflective metallic material, also may be used.

Probe 900 also includes a maternal ECG electrode 920 mounted flush with rear surface 921 of outer body 923 for providing a maternal ECG signal, and for providing a fetal ECG signal in conjunction with fetal ECG electrode 916. Gasket 922 serves the dual purposes of attaching the probe to the fetal surface, and of electrically insulating fetal ECG electrode 916 from maternal ECG electrode 920. A sealant also may be used as described above to improve the sealing quality of gasket 922.

Figure 10A:
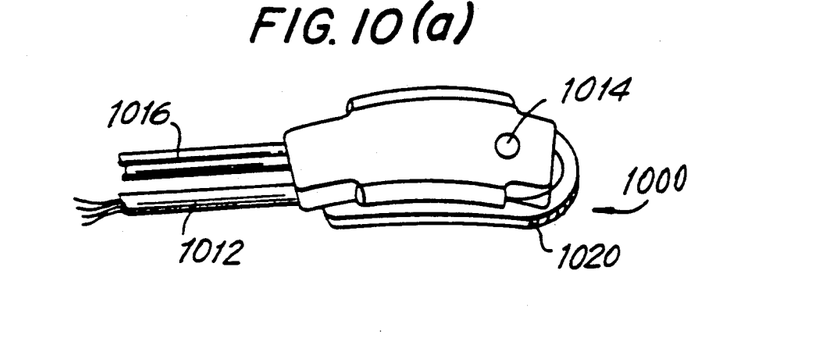
FIGS. 10(a)-(b) are top plan and bottom perspective views of a seventh embodiment of the probe of the present invention.
Figure 10B:
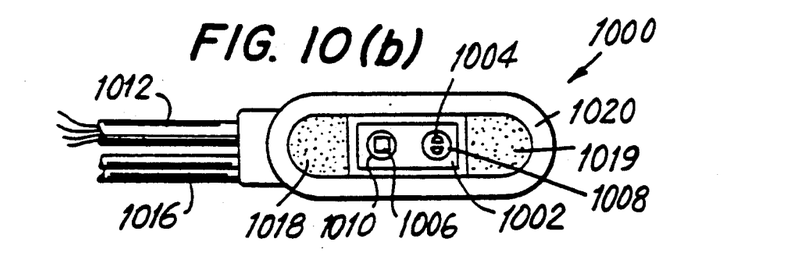

FIGS. 10(a)-(b) show top and bottom views of an intrauterine sensor 1000 in which an electrically conductive block 1002, formed from metal or metal-impregnated silicone, serves the multiple purposes of focusing and directing light from light sources 1004 toward the fetal tissue surface, of minimizing the amount of shunted light detected by photodetector 1006, of focusing and directing light from the fetal tissue surface toward photodetector 1006, and of providing an electrically conductive surface suitable for a fetal ECG sensor.

Block 1002 is mounted on the substrate on which light sources 1004 and photodetector 1006 are mounted, and is aligned such that openings 1008 and 1010 are positioned directly over light sources 1004 and photodetector 1006, respectively, to provide reflective surfaces for coupling light between blood-perfused fetal tissue and the probe more efficiently. Electrical cable 1012 includes wires for providing separate electrical connection to light sources 1004, photodetector 1006, fetal ECG electrode 1002, and maternal ECG electrode 1014. As in previously described embodiments, double-lumen vacuum and vent tubes 1016 provide pneumatic connections to the cavity (not shown) or probe 1000, the exposed portions of which are covered by open cell silicone foam filter pads 1018 and 1019 attached to probe 1000, the gasket 1020 operates to form a seal with the fetal surface.

FIGS. 11(a)-(b) show top and cross-sectional side views of a preferred embodiment of an intrauterine probe 1100. As in previously described embodiments, probe 1100 includes light sources 1102 and photodetector 1104 mounted on and electrically connected to substrate 1106, which in turn is supported by inner boot 1108 and has electrical leads (not shown) for connection to wires (also not shown) in electrical cable 1110 for connection to an external pulse oximeter. A maternal ECG electrode 1112 is mounted through a hole in the rear surface of outer body 1114, and is electrically connected at its inner surface 1113 to a wire (not shown) in electrical cable 1110. Outer body 1114 includes cavity 1116 to which vacuum pressure is applied by a vacuum pump (not shown) through vacuum tube 1118 which is connected to cavity 1116 through conduit 1120. Outer body 1114 also includes separate parallel conduits (not shown) for receiving vent tube 1122 and electrical cable 1110.

Light sources 1102 and photodetector 1104 are separated by an opaque barrier block 1124 mounted on substrate 1106. Barrier block 1124 comprises a conductive material such as metal or impregnated silicone rubber, and includes two circular openings 1126 and 1128 positioned respectively above light sources 1102 and photodetector 1104 for transmitting light between the fetal tissue surface and the optical devices. Openings 1126 and 1128 have reflective walls for focusing the transmitted light. Preferably, opening 1126 slopes inwardly at the bottom to reflect transversely emitted light. Openings 1126 and 1128 are filled with a clear encapsulant such as epoxy or silicone rubber on top of which are located protrusions 1130 and 1132 and conductive mask 1134.

Protrusions 1130 and 1132 have smoothly rounded upper surfaces, and are made from a hard, light-transmissive material such as clear epoxy, although softer clear materials such as silicone rubber can also be used. Protrusions 1130 and 1132 may be formed as part of the encapsulant filling openings 1126 and 1128, or as separate pieces mounted on top of the encapsulant. Protrusions 1130 and 1132 extend through openings in conductive mask 1134 above rim 1136 of outer body 1114 to which gasket 1138 is attached.

Protrusions 1130 and 1132 serve the purpose of imposing a dimpled counter on the fetal tissue surface. As discussed earlier, the dimpling effect facilitates coupling light to and from blood-perfused portions of the fetal tissue, and prevents light from being shunted directly from light sources 1102 to photodetector 1104 as a result of any mismatch between the curvature of the fetal tissue surface and the probe surface. The perfusion of blood in the fetal tissue between the optical devices can be increased by making an area of the surface of barrier block 1124 concave, such that blood-perfused fetal tissue fills the concave area between the optical devices when the probe is secured to the fetal tissue surface.

Gasket 1138 has a substantially rectangular cross-section and is supported by rim 1136 such that the top surface of the gasket is elevated at its outer edge as shown in FIG. 11(a). Gasket 1138 may have other cross-sectional shapes (e.g., triangular, with the outer edge being the thicker edge), although it may be more difficult to manufacture compliant gaskets in such shapes.

Conductive mask 1134 is electrically connected to barrier block 1124 to form a fetal ECG electrode. Preferably, conductive mask comprises a thin sheet of soft metal the edges of which are curved downward as shown to eliminate sharp edges. Barrier block 1124 is connected to a wire (not shown) of electrical cable 1110 for connecting the metal ECG electrode to an external ECG monitor. Caps between the fetal ECG electrode and the inner walls of outer body 1114 are covered with open-cell foam pads 1139 and 1140 to provide a filtered vacuum port between cavity 1116 and the fetal tissue surface.

Although probe 1100 is shown without curvature, it is to be understood that this is for purposes of illustration only. As discussed with respect to previously illustrated embodiments, outer body 1114 of probe 1100 is molded or bent (as by insertion of a curved wire in receptacles 1142 and 1144) to provide a concave curvature closely approximating the curvature of the desired point of placement on the fetus (e.g., the head).

If desired, probe 1100 can be modified to increase the amount of light reaching detector 1104 by eliminating protrusion 1132 and increasing the diameter of the opening in mask 1134 above the photodetector. The amount of light transmitted between the optical devices and the blood perfused fetal tissue also can be increased by bringing the optical devices closer to the fetal tissue surface. This can be achieved, for example, by mounting the optical devices on a thick substrate and by reducing the thickness of barrier block 1124. Also, for purposes of simplifying the manufacture of probe 1100, the diameter of opening 1128 in barrier block 1124 can be made equal to the diameter of protrusion 1130, such that conductive mask 1134 may be eliminated.

The above-described probe embodiments may include additional sensing devices such as, in FIG. 9(a), a thermistor 924 and a heat flux sensor 926 adapted to provide electrical signals to external monitoring equipment (not shown) for measuring the temperature of and heat flux at a portion of the fetal tissue surface or the maternal tissue fluids, in accordance with temperature and heat flux measuring techniques. A second pair of light sources 906 and photodetectors 908 may be provided on the rear surface of the probe for measuring blood flow characteristics of the uterine tissue, including but not limited to blood oxygen saturation of hemoglobin in arterial blood, volume of individual blood-pulsations supplying the tissue, and the rate of blood pulsations corresponding to each maternal heart beat. In such an arrangement, the maternal light source-photodetector pair wound preferably operate at different wavelengths than the fetal light source-photodetector pair.

One skilled in the art will appreciate that the present invention can be practiced by other than the described embodiments, which are presented for purposes of illustration and not of limitation, and the present invention is limited only by the claims which follow.

What is claimed is:

1. An intrauterine sensor system, comprising:
   a probe adapted for insertion into a uterus, the probe having a deformable outer body;
   means for connecting the probe to a vacuum source to positively attach the probe to the fetal tissue surface;
   means for forming a deformable seal, the deformable seal means being mounted to a surface of the outer body that contacts the fetal tissue surface having a compliancy greater than the compliancy of the fetal tissue;
   a light source and a light detector mounted in the probe and adapted to generate a signal for use in measuring at least one fetal blood flow characteristic by pulse oximetry;
   first electrode means for detecting a fetal body function and for generating a signal responsive to the detected body function, the first electrode means being mounted in the probe and adapted to contact the fetal tissue surface when the probe is in place; and
   means for connecting the light source to an external source of power, and for connecting the light detector and the first electrode means to external components adapted to receive and monitor the signals generated by the light detector and the first electrode means.

2. The intrauterine sensor system of claim 1, wherein the deformable outer body comprises a flexible diaphragm having a pocket formed therein in which the light source and light detector are disposed.

3. The sensor system of claim 1, wherein the deformable seal means comprises a gasket secured to the outer body.

4. The sensor system of claim 3, further comprising:
   second electrode means associated with the probe for detecting a body function and for generating a signal responsive to the detected body function; and
   means for connecting the second electrode means to external components adapted to receive and monitor the signal generated by the second electrode means.

5. The sensor system of claim 4, further comprising:
   a second light source and a second light detector, mounted on a surface of the probe directed toward the uterine wall when the probe is in place and adapted to generate a signal for use in measuring at least one maternal blood flow characteristic by pulse oximetry; and
   means for connecting the second light source to an external source of power, and for connecting the second light detector to external components adapted to receive and monitor the signal generated by the second light detector.

6. The sensor system of claim 5, further comprising:
   temperature sensing means mounted in the probe for sensing the temperature of a portion of the fetal tissue surface and for generating a signal responsive to the sensed temperature; and
   means for connecting the temperature sensing means to external components adapted to receive and monitor the signal generated by the temperature sensing means.

7. The sensor system of claim 6, further comprising:
   means mounted in the probe for sensing heat flux in at least a portion of one of the maternal biological fluid and the fetal tissue surface and for generating a signal responsive to the sensed heat flux; and
   means for connecting the heat flux sensing means to external components adapted to receive and monitor the signal generated by the heat flux sensing means.

8. The sensor system of claim 1, wherein the probe further includes a light barrier element between the light source and the light detector.

9. The sensor system of claim 1, wherein the first electrode means is mounted between the light source and the light detector as a light barrier.

10. The sensor system of claim 1, wherein the probe further includes a first reflector being mounted adjacent one of the light source and the light detector.

11. The sensor system of claim 10, wherein the first reflector is mounted as a light barrier element between the light source and the light detector.

12. The sensor system of claim 1, wherein the first electrode means is a reflector mounted adjacent one of the light source and the light detector.

13. The sensor system of claim 1, wherein the first electrode means is a reflector mounted adjacent one of the light source and the light detector, and is positioned as a light barrier element between the light source and the light detector.

14. The sensor system of claim 13, wherein the first reflector means reflects light between the light source and the fetal tissue surface, and the probe further includes a second reflector means for reflecting light between the light detector and the fetal tissue surface, and wherein the first and second reflector means are formed by a single electrically conductive element.

15. The sensor system of claim 14, wherein the first and second reflector means are flexible.

16. The sensor system of claim 1, further including at least one porous filter element mounted on the probe for diffusing air removed from within the probe before the air enters the means connecting the probe to the vacuum source.

17. The sensor system of claim 16, wherein the first electrode means comprises a conductive surface which is urged against the fetal tissue surface by the porous filter element.

18. The sensor system of claim 1, wherein the first electrode means comprises a spring-loaded electrically conductive surface biased toward the fetal tissue surface.

* * * * *